(12) United States Patent
Crabbs

(10) Patent No.: US 10,570,339 B2
(45) Date of Patent: Feb. 25, 2020

(54) METHOD, APPARATUS, AND SYSTEM FOR PROVIDING AN INTEGRATED BIOENERGY COMPLEX TO PROCESS MIXED SOLID WASTE

(71) Applicant: IBC Techs, LLC, Fairfax Station, VA (US)

(72) Inventor: Ray Crabbs, Fairfax Station, VA (US)

(73) Assignee: IBC TECHS, LLC, Fairfax Station, VA (US)

( * ) Notice: Subject to any disclaimer, the term of this patent is extended or adjusted under 35 U.S.C. 154(b) by 0 days.

(21) Appl. No.: 15/894,479

(22) Filed: Feb. 12, 2018

(65) Prior Publication Data
US 2019/0249090 A1    Aug. 15, 2019

(51) Int. Cl.
*C10G 9/00* (2006.01)
*C10L 1/04* (2006.01)
(Continued)

(52) U.S. Cl.
CPC .............. *C10G 9/00* (2013.01); *A61L 2/04* (2013.01); *C07C 7/04* (2013.01); *C07C 29/80* (2013.01);
(Continued)

(58) Field of Classification Search
CPC . C10G 9/00; C10G 73/00; C10G 7/00; C10G 240/08; C10G 240/04;
(Continued)

(56) References Cited

U.S. PATENT DOCUMENTS 7,216,593 B2    5/2007    Capote et al.
7,772,453 B2    8/2010    Cerroni
(Continued)

FOREIGN PATENT DOCUMENTS

CN    101433904 A    5/2009

OTHER PUBLICATIONS

Notification of Transmittal of the International Search Report and the Written Opinion of the International Searching Authority, or the Declaration; International Search Report and Written Opinion of the International Searching Authority for corresponding International Patent Application PCT/US2019/016653, dated Mar. 27, 2019, 10 pages.

*Primary Examiner* — Jafar F Parsa
(74) *Attorney, Agent, or Firm* — Ditthavong & Steiner, P.C.

(57) ABSTRACT

An approach is provided for processing mixed solid waste using an integrated bioenergy complex. The approach, for instance, involves receiving the mixed solid waste at the integrated bioenergy complex, the integrated bioenergy complex including an organic conversion processing center and an inorganic conversion processing center. The approach also involves separating the mixed solid waste into recyclables, an organic waste stream, and an inorganic waste stream. The approach further involves feeding the organic waste stream to the organic conversion processing center to produce organic conversion products and an organic residual, and feeding the organic residual and the inorganic waste stream to the inorganic conversion processing center to produce inorganic conversion products, electric power, and a residual waste. The electric power is used to partially or fully power the organic conversion processing center, and residual waste is less than a target percentage of the received mixed solid waste.

14 Claims, 12 Drawing Sheets

(51) Int. Cl.
| | |
|---|---|
| *C10L 1/02* | (2006.01) |
| *C07C 7/04* | (2006.01) |
| *C07C 29/80* | (2006.01) |
| *C10G 7/00* | (2006.01) |
| *C10G 73/00* | (2006.01) |
| *A61L 2/04* | (2006.01) |
| *C10G 1/02* | (2006.01) |
| *C10G 1/10* | (2006.01) |
| *C10G 1/00* | (2006.01) |

(52) U.S. Cl.
CPC ............... *C10G 1/002* (2013.01); *C10G 1/02* (2013.01); *C10G 1/10* (2013.01); *C10G 7/00* (2013.01); *C10G 73/00* (2013.01); *C10L 1/02* (2013.01); *C10L 1/04* (2013.01); *C10G 2300/1003* (2013.01); *C10G 2300/1014* (2013.01); *C10G 2400/02* (2013.01); *C10G 2400/04* (2013.01); *C10G 2400/08* (2013.01); *C10L 2200/0469* (2013.01); *C10L 2270/023* (2013.01); *C10L 2270/026* (2013.01); *C10L 2270/04* (2013.01)

(58) Field of Classification Search
CPC .......... C10G 240/02; C10G 2300/1014; C10G 2300/1003; C10L 1/02; C10L 1/04; C10L 2270/04; C10L 2270/026; C10L 2270/023; C10L 2270/0469
See application file for complete search history.

(56) References Cited

U.S. PATENT DOCUMENTS

| | | | |
|---|---|---|---|
| 9,650,650 B2* | 5/2017 | Gitschel | ................... C10G 1/10 |
| 2007/0272131 A1 | 11/2007 | Carabin et al. | |
| 2008/0166265 A1 | 7/2008 | Day | |
| 2013/0300121 A1* | 11/2013 | Ali | ........................ F23G 5/0276 290/52 |

* cited by examiner

METHOD, APPARATUS, AND SYSTEM FOR PROVIDING AN INTEGRATED BIOENERGY COMPLEX TO PROCESS MIXED SOLID WASTE

BACKGROUND

The composition of mixed solid waste can be highly variable between different types of waste streams (e.g., commercial and demolition, municipal solid waste, electronic waste, etc.) as well as within a single type of waste stream (e.g., municipal solid waste can vary depending on collection location, time of collection, etc.). This high variability has historically made it difficult for solid waste recycling and disposal facilities to process mixed solid waste without leaving considerable amounts of residual wastes that, for instance, are either too difficult or too expensive to recycle or recover. The residual waste would traditionally have to be disposed through means other than recycling or recovery (e.g., landfilling, incineration, etc.), which can create environmental or sustainability concerns. As a result, waste management providers face significant technical challenges to reducing residual wastes resulting from processing mixed solid waste.

SOME EXAMPLE EMBODIMENTS

Therefore, there is a need for an approach for increasing the efficiency of mixed solid waste recycling/recovery, and reducing residual waste.

According to one embodiment, a method comprises receiving mixed solid waste at an integrated bioenergy complex. The integrated bioenergy complex, for instance, includes an organic conversion processing center (e.g., a liquid fuels plant) and an inorganic conversion processing center (e.g., an insulation/power plant). The method also comprises separating the mixed solid waste into an organic waste stream and an inorganic waste stream. In some embodiments, recyclables can be extracted from the mixed solid waste, the organic waste stream, and/or the inorganic waste stream prior to further processing. The method then further comprises feeding the organic waste stream (or a non-recycled portion of the organic waste stream for embodiments in which recyclables are extracted) to the organic conversion processing center to produce one or more organic conversion products and an inorganic residual. The method further comprises feeding the inorganic residual and the inorganic waste stream (or a non-recycled portion of the inorganic waste stream for embodiments in which recyclables are extracted) to the inorganic conversion processing center to produce one or more inorganic conversion products, electric power (e.g., "green" electric power), and a residual waste. The electric power is used to partially or fully power the organic conversion processing center, and the residual waste is less than a target percentage (e.g., 3-5%) of the received mixed solid waste.

According to one embodiment, a system comprises an integrated bioenergy complex configured to process mixed solid waste to achieve a blended moisture content less than or equal to a target moisture percentage (e.g., 10%), and to separate the mixed solid waste into an organic waste stream and an inorganic waste stream. In some embodiments, recyclables can be extracted from the mixed solid waste, the organic waste stream, and/or the inorganic waste stream prior to further processing. The system also comprises an organic conversion processing center (e.g., employing a thermal conversion process) located at the bioenergy complex, the organic conversion processing center configured to receive the organic waste stream (or a non-recycled portion of the organic waste stream for embodiments in which recyclables are extracted) to produce one or more organic conversion products and an inorganic residual. The system further comprises an inorganic conversion processing center (e.g., employing an induction conversion process/plasma converter) located at the bioenergy complex, the inorganic conversion processing center configured to receive the inorganic residual and the inorganic waste stream (or a non-recycled portion of the inorganic waste stream for embodiments in which recyclables are extracted) to produce one or more inorganic conversion products, electric power (e.g., "green" electric power), and a residual waste. The electric power is used to partially or fully power the organic conversion processing center, and the residual waste is less than a target percentage (e.g., 3%) of the received mixed solid waste.

According to another embodiment, an apparatus comprises one or more components configured to receive mixed solid waste at a bioenergy complex. The bioenergy complex, for instance, includes an organic conversion processing center and an inorganic conversion processing center. The apparatus is also configured to separate the mixed solid waste into an organic waste stream and an inorganic waste stream. In some embodiments, recyclables can be extracted from the mixed solid waste, the organic waste stream, and/or the inorganic waste stream prior to further processing. The apparatus is then further configured to feed the organic waste stream (or a non-recycled portion of the organic waste stream for embodiments in which recyclables are extracted) to the organic conversion processing center to produce one or more organic conversion products and an inorganic residual. The apparatus is further configured to feed the inorganic residual and the inorganic waste (or a non-recycled portion of the inorganic waste stream for embodiments in which recyclables are extracted) to the inorganic conversion processing center to produce one or more inorganic conversion products, electric power (e.g., "green" electric power), and a residual waste. The residual waste is less than 3% of the received mixed solid waste.

According to another embodiment, an apparatus comprises means for receiving mixed solid waste at an integrated bioenergy complex. The integrated bioenergy complex, for instance, includes an organic conversion processing center and an inorganic conversion processing center. The apparatus also comprises means for separating the mixed solid waste into an organic waste stream and an inorganic waste stream. In some embodiments, recyclables can be extracted from the mixed solid waste, the organic waste stream, and/or the inorganic waste stream prior to further processing. The apparatus further comprises means for feeding the organic waste stream (or a non-recycled portion of the organic waste stream for embodiments in which recyclables are extracted) to the organic conversion processing center to produce one or more organic conversion products and an organic residual. The apparatus further comprises means for feeding the inorganic residual and the inorganic waste stream (or a non-recycled portion of the inorganic waste stream for embodiments in which recyclables are extracted) to the inorganic conversion processing center to produce one or more inorganic conversion products, electric power (e.g., "green" electric power), and a residual waste. The electric power is used to partially or fully power the organic conversion processing center, and the residual waste is less than a target percentage (e.g., 3%) of the received mixed solid waste.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings.

DESCRIPTION OF SOME EMBODIMENTS

Examples of a method, apparatus, and system for providing an integrated bioenergy complex to process mixed solid waste are disclosed. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Figure 1:
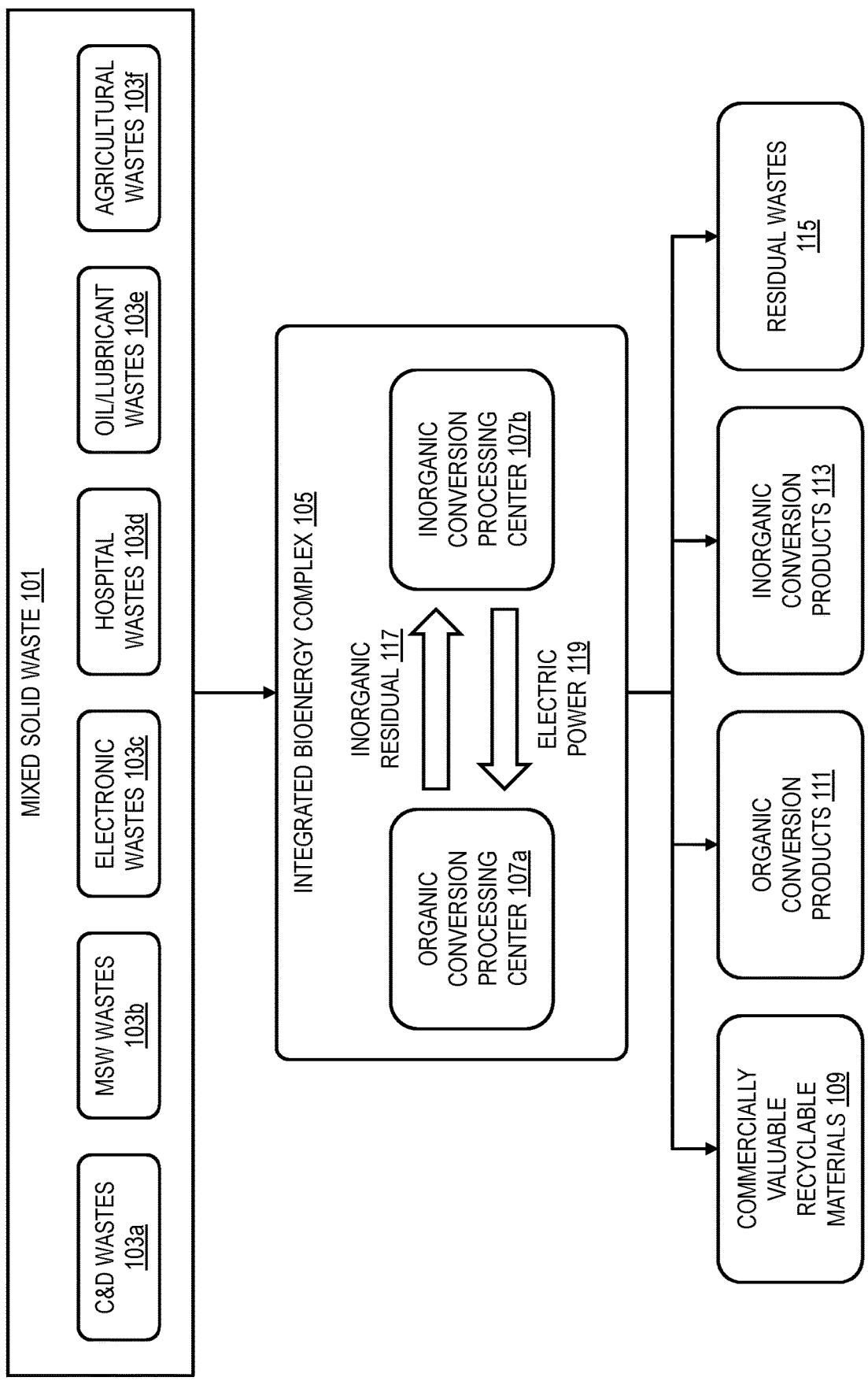
FIG. 1 is a diagram of a system capable of providing an integrated bioenergy complex to process mixed solid waste, according to one embodiment.

FIG. 1 is a diagram of a system capable of providing an integrated bioenergy complex to process mixed solid waste, according to one embodiment. Mixed solid waste 101 is being generated at ever increasing rates across many sectors (e.g., commercial and demolition (C&D) waste 103$a$, municipal solid waste (MSW) 103$b$, electronic waste 103$c$, hospital waste 103$d$, oil/lubricant wastes 103$e$, agricultural wastes 103$f$, and/or wastes from any other sector). The term mixed solid waste, for instance, refers to wastes that have not been sorted or separated, and contain a composite of different types of wastes including, but not limited to, any combination of: biodegradable wastes (e.g., food, paper, vegetation, etc.), recyclable wastes (e.g., metals, bottles, cans, etc.), inert wastes (e.g., C&D wastes, dirt, rock, debris, etc.), electronic wastes (e.g., computers, electronic devices, appliances, etc.), composite wastes (e.g., toys containing many different components, waste clothing, etc.), biomedical wastes (e.g., pharmaceutical drugs, used hospital supplies, hospital instruments, etc.), and the like.

Traditionally, waste management facilities have managed mixed solid waste 101 by using processes such as recycling, composting, disposal, and waste-to-energy processes. However, as discussed above, because of the wide variability in the composition of mixed solid waste 101, waste management facilities face significant technical challenges with using these traditional processes to process mixed solid waste 101 without generating significant amounts of residual wastes and airborne contaminants. For example, with respect to recycling, waste management facilities often use sorting to identify and pick out recyclable materials from a waste steam. However, depending on the material and the sorting technique (e.g., manual labor, automated sorting, etc.), it can be difficult to achieve 100% sorting efficiency, thereby leaving considerable amounts of recyclable materials in the residual waste. In addition, the cost and effort needed to achieve higher levels of recyclable recovery can exceed the commercial value of the recovered recyclable material, thereby increasing the likelihood that a waste management facility would not employ extra efforts to reduce residual wastes. Traditional waste management facilities would then typically dispose of the residual wastes in landfills, through incineration, or other equivalent means. This type of disposal generally has increased environmental impacts and costs (e.g., landfill costs, transport and storage costs of the residual wastes, landfill gas emissions into the atmosphere, etc.).

To address these challenges, the system 100 of FIG. 1 introduces an integrated waste management facility (e.g., the integrated bioenergy complex 105) in which a panoply of technologies (e.g., waste-stream recycling, recovery, and/or processing technologies) are co-located to achieve a high recycle/recovery rate of incoming waste streams in a cost-efficient system. In one embodiment, the integrated bioenergy complex 105 receives incoming mixed solid waste 101 comprised of any combination of C&D wastes 103$a$, MSW wastes 103$b$, electronic wastes 103$c$, hospital wastes 103$d$, and oil/lubricant wastes 103$e$. The integrated bioenergy complex 105 then separates the mixed solid waste 101 into organic and inorganic waste streams which are then fed respectively to an organic conversion processing center 107$a$ and an inorganic conversion processing center 107$b$. In one embodiment, the bioenergy complex can also extract commercially valuable recyclable materials 109 from the mixed solid waste 101 and/or the organic and inorganic waste streams before the streams are fed to the organic conversion processing center 107a or the inorganic conversion processing center 107a.

In one embodiment, the organic conversion processing center 107a includes technologies (e.g., a liquid fuels plant using thermal conversion or catalytic cracking, or equivalent) for converting the organic waste stream into organic conversion products 111 (e.g., fuels, industrial solvents, Fischer-Tropsch (F-T) waxes, etc.) that can be recovered and/or recycled. Similarly, the inorganic conversion processing center 107b includes technologies (e.g., an insulation/power plant using an induction furnace and plasma converter, or equivalent) for converting the inorganic waste stream into inorganic conversion products 113 (e.g., rock wool, metal ingots, etc.). Both the organic conversion processing center 107a and the inorganic conversion processing center 107b are co-located at the integrated bioenergy complex 105.

In one embodiment, to reduce the overall residual wastes 115 from the entire bioenergy complex 105, intermediate residual wastes from each of the centers 107a and 107b can be cross-fed as feedstock into the other center. For example, inorganic residual 117 can be fed to the inorganic conversion processing center 107b (or vice versa) to advantageously improve recovery efficiency. In one embodiment, the cross-feeding of residuals as feedstock can be performed recursively until a target residual waste percentage is achieved (e.g., 3-5% or any other specified target). In yet another embodiment, conversion products (e.g., organic conversion products 111 and inorganic conversion products 113) can be cross-feed between the centers 107a and 107b to support their respective operations. For example, electric power 119 generated by the inorganic conversion processing center 107b (e.g., via its insulation/power plant) can be delivered to the organic conversion processing center 107a to support its operations (e.g., the liquid fuels plant). In one embodiment, the electric power 119 can be referred to as "green" electric power to indicate that the inorganic conversion processing center 107b uses best in class power generation technologies that result in minimal or low impacts (e.g., by sequestering $CO_2$ equivalents into conversion products, thereby minimizing the release of $CO_2$ and/or other residual wastes into the environment during the electric power generation process).

Figure 2:
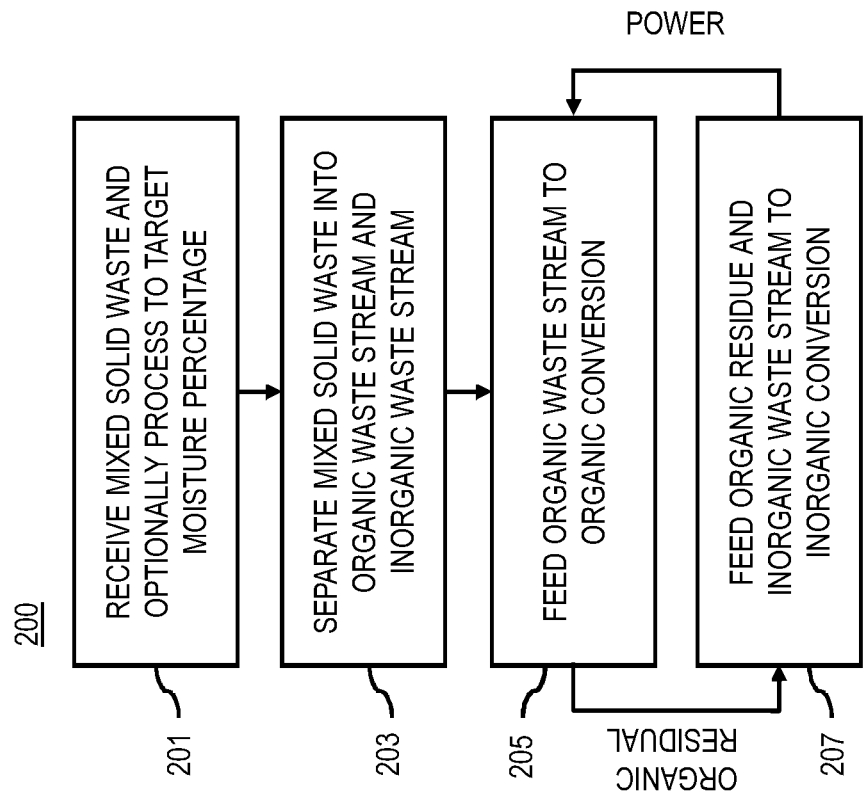
FIG. 2 is a flowchart of a process for processing mixed solid waste at an integrated bioenergy complex, according to one embodiment.

FIG. 2 is a flowchart of a process for processing mixed solid waste at an integrated bioenergy complex, according to one embodiment. FIG. 2 describes one general embodiment of the operations of the integrated bioenergy complex 105 and discussed with respect to the example components of the integrated bioenergy complex 105 illustrated in FIG. 3. Specific embodiments corresponding to each of the different types of mixed solid waste 101 (e.g., C&D wastes 103a, MSW wastes 103b, electronic wastes 103c, hospital wastes 103d, and oil/lubricant wastes 103e) are described in more detail with respect to FIGS. 6-10 respectively).

Figure 3:
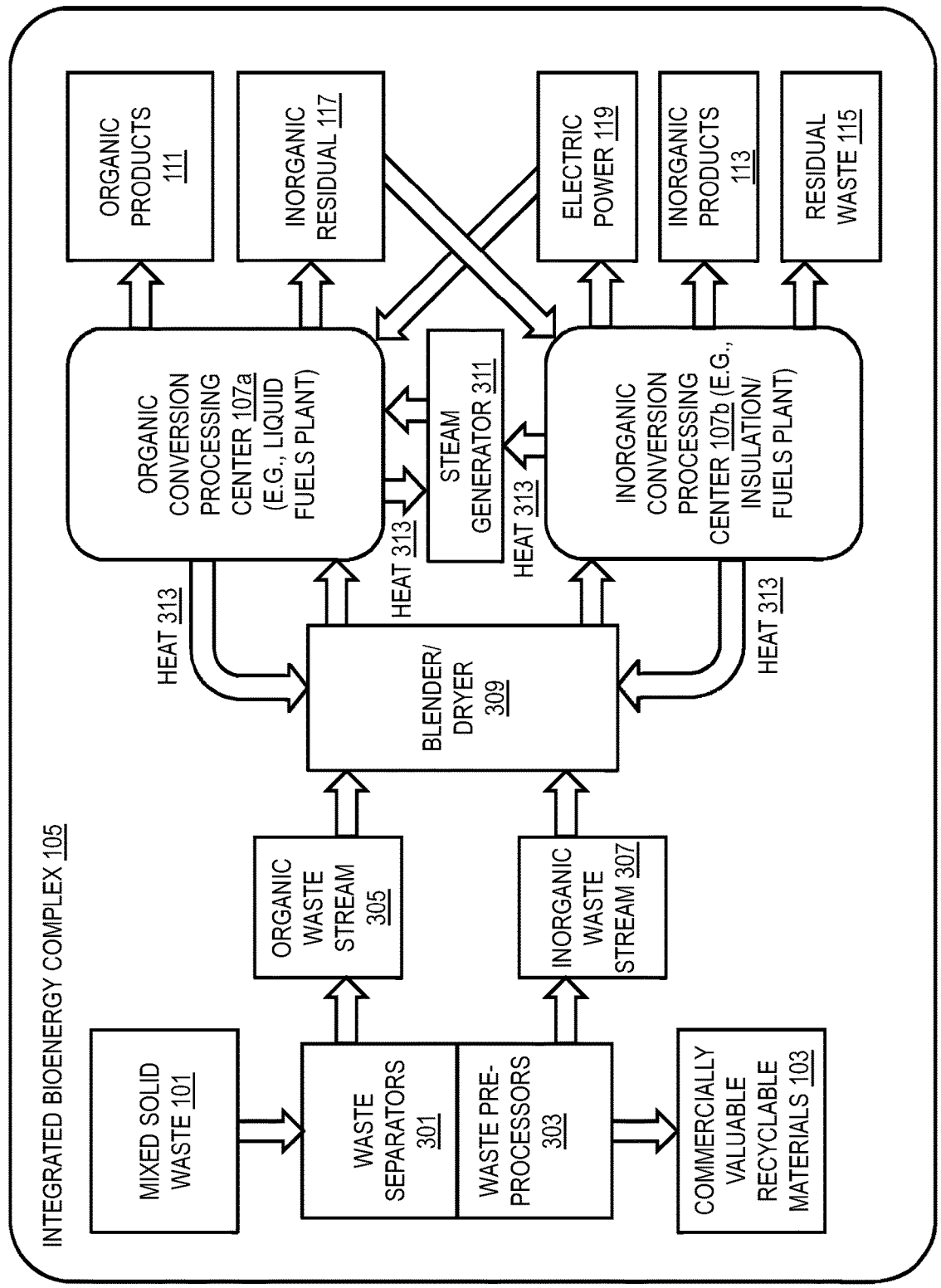
FIG. 3 is a diagram illustrating components of an integrated bioenergy complex for processing mixed solid waste, according to one embodiment.

In one embodiment, as shown in FIG. 3, the integrated bioenergy complex 105 includes the following components for processing mixed solid waste 101: waste separators 301, waste pre-processors 303 (e.g., shredders, grinders, etc.), blender/dryer 309, steam generator 311, in addition to components of the integrated bioenergy complex 105 described with respect to FIG. 1 (e.g., mixed solid waste 101), organic conversion processing center 107a), inorganic conversion processing center 107b, organic conversion products 111, inorganic conversion products 113, residual waste 115, inorganic residual 117, and electric power 119). As such, the integrated bioenergy complex 105 and/or any of its component as depicted in FIGS. 1 and 3 can provide means for accomplishing various parts of the process 200 of FIG. 2, as well as means for accomplishing embodiments of other processes described herein.

In one embodiment, the integrated bioenergy complex 105 occupies a geographic area sufficient for co-locating all of the described components as well as facilities for receiving mixed solid waste 101 and for storing and/or transporting any of the products/recyclables resulting from the process 200. In addition, it is contemplated that the integrated bioenergy complex 105 can employ any means to transport materials between the components of the integrated bioenergy complex 109 including, but not limited to conveyors, haul vehicles, slides, pipes, transmission lines, etc.

In step 201, the integrated bioenergy complex 105 receives mixed solid waste 101 for processing. By way of example, the integrated bioenergy complex 105 can be located near to existing transportation hubs that can support commercial traffic under one or more modes of transportation (e.g., trucks, trains, ships/water vessels, airplanes, etc.). In one embodiment, the integrated bioenergy complex 105 includes an organic conversion processing center 107a and an inorganic conversion processing center 107b. As discussed above, the centers 107a and 107b can synergistically and/or recursively process the intermediate residual wastes originating from the other center to reduce the total residual waste 115 resulting from operation of the integrated bioenergy complex 105.

Figure 4:
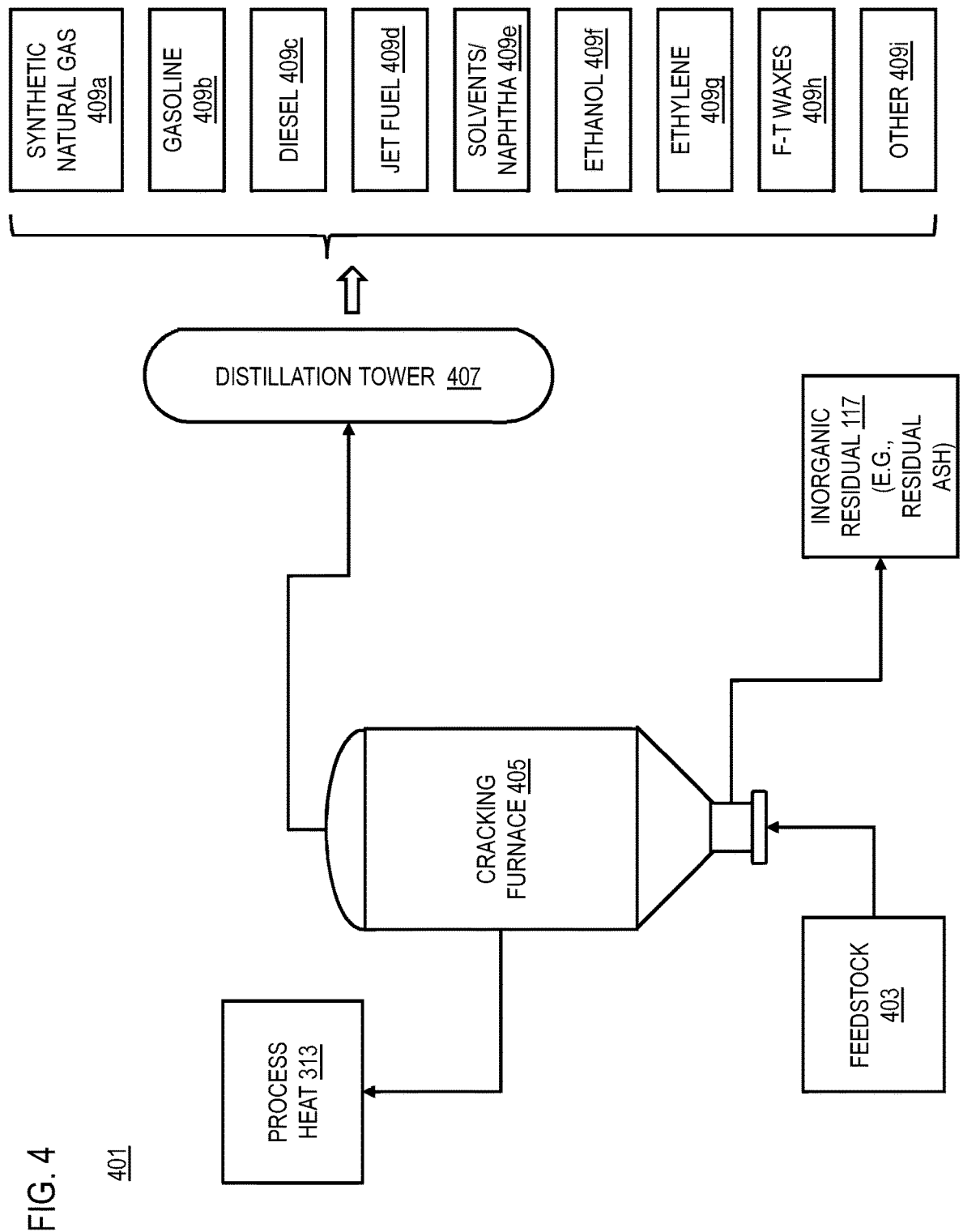
FIG. 4 is a diagram of an example organic conversion processing center including a liquid fuels plant for processing organic waste streams, according to one embodiment.

In one embodiment, the organic conversion processing center 107a includes a liquid fuels plant to convert organic wastes into products for recycling and recovery. FIG. 4 illustrates an example liquid fuels plant 401 that can be included in the organic conversion processing center 107a. It is noted that the liquid fuels plant 401 and the thermal conversion process which it employs are provided by way of illustration and not as a limitation. It is contemplated that any organic conversion process, including non-thermal processes, that results in recyclable or recoverable products can be used according to the embodiments described herein.

As shown FIG. 4, in one embodiment, the liquid fuels plant 401 uses a thermal cracking process to convert feedstock 403 (e.g., organic wastes or material) into fuels or other organic conversion products 111. The thermal cracking process uses a cracking furnace 405 to heat the feedstock 403 under high temperature to break large carbon molecules into smaller carbon molecules that can be collected or used to a variety of organic conversion products. The specific products that are generated can be controlled through temperature or by the addition of specific catalysts to promote formation of target molecules. For example, the catalysts can be used to promote the formation of petroleum based products. In this case, products with a lower boiling point are released first, and higher boiling point molecules being released later.

These products, for instance, can then be captured using a distillation tower 407 as they are released from the cracking furnace 405. In this way, various products such as, but not limited to, synthetic natural gas 409a, gasoline 409b, diesel 409c, jet fuel 409d, solvents/naphtha 409e, ethanol 409f, ethylene 409g, F-T waxes 409h, and other similar compounds 409i can be produced from the feedstock. The residual ash remaining in the cracking furnace 403 after completing the thermal cracking process ends constitutes the inorganic residual 117. In one embodiment, the products 409a-409i are examples of the organic conversion products 111 produced by the organic conversion processing center 107a.

Figure 5:
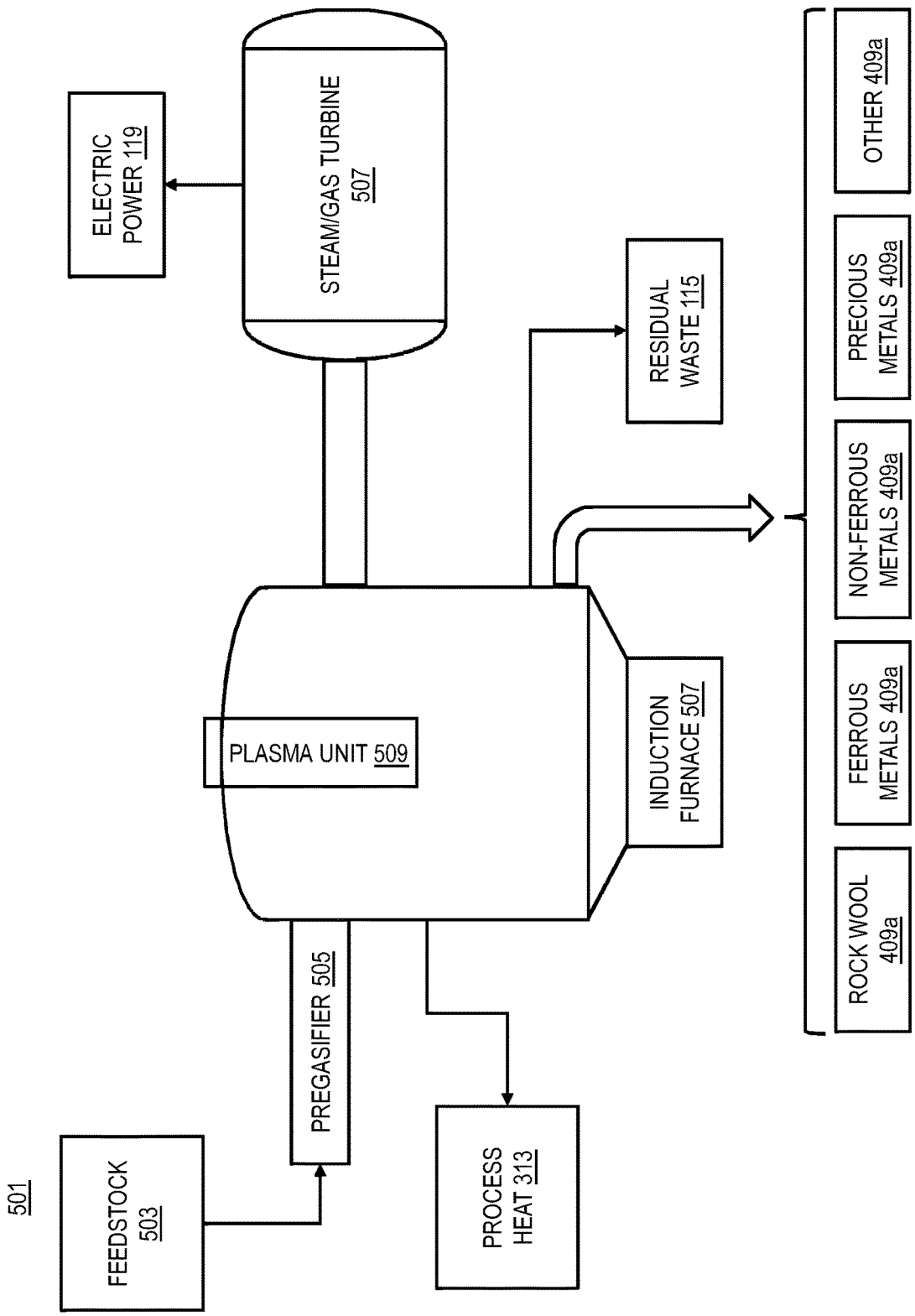
FIG. 5 is a diagram of an example inorganic conversion processing center including an induction conversion process/plasma converter for processing inorganic waste streams, according to one embodiment.

In one embodiment, the inorganic conversion processing center 107b includes an insulation/power plant to convert inorganic wastes into various inorganic conversion products. FIG. 5 illustrates an example insulation/power plant 501 that can be included in the organic conversion processing center 107a. As with example above, it is noted that the insulation/power plant 501 and the induction conversion/plasma converter process which it employs are provided by way of illustration and not as a limitation. It is contemplated that any inorganic conversion process that results in recyclable or recoverable products and generates electric power can be used according to the embodiments described herein.

As shown FIG. 5, in one embodiment, the insulation/power plant 501 uses an induction conversion/plasma converter process to convert feedstock 503 (e.g., inorganic waste or material) into various inorganic conversion products 113. For example, the feedstock 503 is introduced into a pregasifier 505 to convert any organic compounds in the feedstock 503 into a gas (e.g., which can be recovered as product fuel or used by the insulation/power plant 501 as fuel for its induction conversion process). After passing through the pregasifier 505, the feedstock 503 is introduced to the induction furnace 507 which is operating at a sufficient temperature for the induction unit 509 to liquify the inorganic material. The intense heat from the induction furnace breaks down any remaining organic compounds through pyrolysis to generate gas and steam. At the same time, inorganic compounds are melted into vitrified mineral slag and molten metal. The steam and/or gas can then be used to produce electric power 119 via a steam/gas turbine 507. On completion of the process, the vitrified mineral slag can be spun into rock wool 509a through a centrifugal process. In addition, any molten metal that has solidified into ingots can be recovered as ferrous metals 509b, non-ferrous metals 509c, and/or precious metals 509d. After removing any other potential products 509e, the remaining material in the induction furnace 507 represents residual waste. When used in the process 200, the residual waste of the induction furnace 507 represents the residual waste 115 of the integrated bioenergy complex 105.

Returning to the process 200 of FIG. 2, in step 203, the waste separators 301 separate the mixed solid waste 101 into an organic waste stream 305 and an inorganic waste stream 307. Although a plasma converter (e.g., as included in the inorganic conversion processing center 107b) traditionally can be used to process the entire mixed solid waste 101 without separating organic or inorganic waste stream, the plasma converter would not be able to produce the range or organic conversion products 111 that the organic conversion processing center 107a is capable of from the organic components of the mixed solid waste 101. Accordingly, by separating the mixed solid waste 101 into the different waste streams 305 and 307, the waste separators 301 advantageously enable the integrated bioenergy complex 105 to make potentially more varied and commercially valuable products.

In one embodiment, the waste separators 301 can use any separation technology known in the art to separate the mixed solid waste 101 into the organic waste stream 305 and the inorganic waste stream 307. The technologies include, but are not limited to, physical screens, density separators, magnetic separators, optical separators, sensor-based separators, long parts separators, air separators, and/or equivalent.

In one embodiment, prior to feeding the organic waste stream to the organic conversion processing center and the inorganic waste stream to the inorganic conversion processing center, the waste separators 301 can extract a recyclable material from the organic waste stream or the inorganic waste stream when a commercial value of the recyclable material is greater than a commercial value threshold. By way of example, the recyclable material includes plastic, paper/cardboard, metals, sand, aggregates, silt, or a combination thereof. In one embodiment, commercial value can be set using any threshold criteria. For example, if the commercial value of extracting the recyclable material exceeds the cost of extracting, processing, transporting, etc. the recyclable material for sale, then the recyclable material can be extracted. Otherwise, the material can remain in the mixed solid waste 101 for processing the processing centers 107a and/or 107b. Another example criteria includes determining whether the recyclable material is needed as feedstock or fuel in any process of the integrated bioenergy complex 105. If the material is needed, then no extraction is performed.

In one embodiment, the integrated bioenergy complex 105 can include waste pre-processors 303 to prepare the mixed solid waste 101, the organic waste stream 305, and/or the inorganic waste stream 307 for subsequent processing. For example, the waste pre-processors 303 can employ any technology known in the art to shred, grind, package, wrap, bale, and/or perform any other steps that might be needed to convey or use the waste 101 or streams 305/307 in subsequent processes of the integrated bioenergy complex 105.

In one embodiment, the integrated bioenergy complex 105 uses thermal conversion, induction conversion, and/or other heat-based technologies to process the mixed solid waste 101. Accordingly, a high moisture content of the mixed solid waste 101, organic waste stream 305, and/or inorganic waste stream 307 can adversely affect the performance of those heat-based technologies. To address this problem, the blender/dryer 309 can process the mixed solid waste 101, organic waste stream 305, and/or inorganic waste stream 307 to achieve a blended moisture content less than or equal to a target moisture percentage. The target moisture percentage can be 10% or other similar range suitable for the processing technology. In one embodiment, the blender/dryer 309 can blend the mixed solid waste or streams 305/307 with dryer material to reduce the overall moisture content. If such blending is not able to achieve the target moisture level, the blender/dryer 309 can use process heat 313 collected from the organic conversion processing center 107a, the inorganic conversion processing center 107b, or a combination thereof to dry the mixed solid waste to achieve the target moisture percentage. In addition or alternatively, the blender/dryer 309 can use any other mechanical means to dry the waste 101 and/or streams 305/307 to the target moisture level.

In step 205, the integrated bioenergy complex 105 feeds the organic waste stream 305 to the organic conversion processing center 107a to produce one or more organic conversion products 111 and the inorganic residual 117. As described above, in one embodiment, the organic conversion processing center 107a includes a liquid fuels plant 401 to produce the one or more organic conversion products 111 from the organic waste stream 305. In this case, the one or more organic conversion products include diesel fuel, jet fuel, organic solvents, naphtha, gasoline, ethanol, ethylene, Fischer-Tropsch waxes, and other similar compounds. In addition, the inorganic residual 117 is ash resulting from the liquid fuels plant.

In step 207, the integrated bioenergy complex 105 feeds the inorganic residual 117 and the inorganic waste stream 307 to the inorganic conversion processing center 107b to produce one or more inorganic conversion products, electric power, and a residual waste. By further processing the inorganic residual 117 through the inorganic conversion processing center 107b, the integrated bioenergy complex 105 can advantageously reduce the overall residual waste 115 by further minimizing the inorganic residual 117. As described above, in one embodiment, the inorganic conversion processing center 107b includes an insulation/power plant 501 to produce the one or more inorganic conversion products 113, electric power 119, residual waste 115, or a combination thereof from the inorganic waste stream 305 and the inorganic residual 117. By way of example, the one or more inorganic conversion products 113 include rock wool, metal ingots, or a combination thereof.

In one embodiment, the integrated bioenergy complex 105 can further optimize its environmental or operational performance by performing any of the steps described below. For example, the integrated bioenergy complex 105 can feed one or more organic conversion products to the inorganic conversion processing center 107b as fuel (e.g., natural gas) for the insulation/power plant 501. This fuel can help maintain the temperature of the plant 501's pregasifier 505, induction furnace 507, etc. In another example, the integrated bioenergy complex 105 can use a thermal process of organic conversion processing center 103 (e.g., the cracking furnace 405 of the liquid fuels plant 401) to sterilize the inorganic waste stream 307 prior to feeding the inorganic waste stream 307 to the inorganic conversion processing center 107b. In this way, if the waste stream 307 is suspected of being biologically contaminated (e.g., hospital or medical wastes), the waste stream 307 can be sterilized so that contamination precautions need not be taken at the inorganic conversion processing center 107b when handling the waste stream 307. In yet another example, the integrated bioenergy complex 105 uses process heat 313 collected from the organic conversion processing center 107a, the inorganic conversion processing center 107b, or a combination thereof to operate a steam generator system 311 to produce electric power. The electric power can then be used onsite or sold back to the public electricity grid.

The description of FIGS. 2-5 above describes embodiments of the integrated bioenergy complex 105 that applies generally to all waste stream types. FIGS. 6-10 describe example applications of the processes of FIGS. 2-5 to specific waste stream types.

Figure 6:
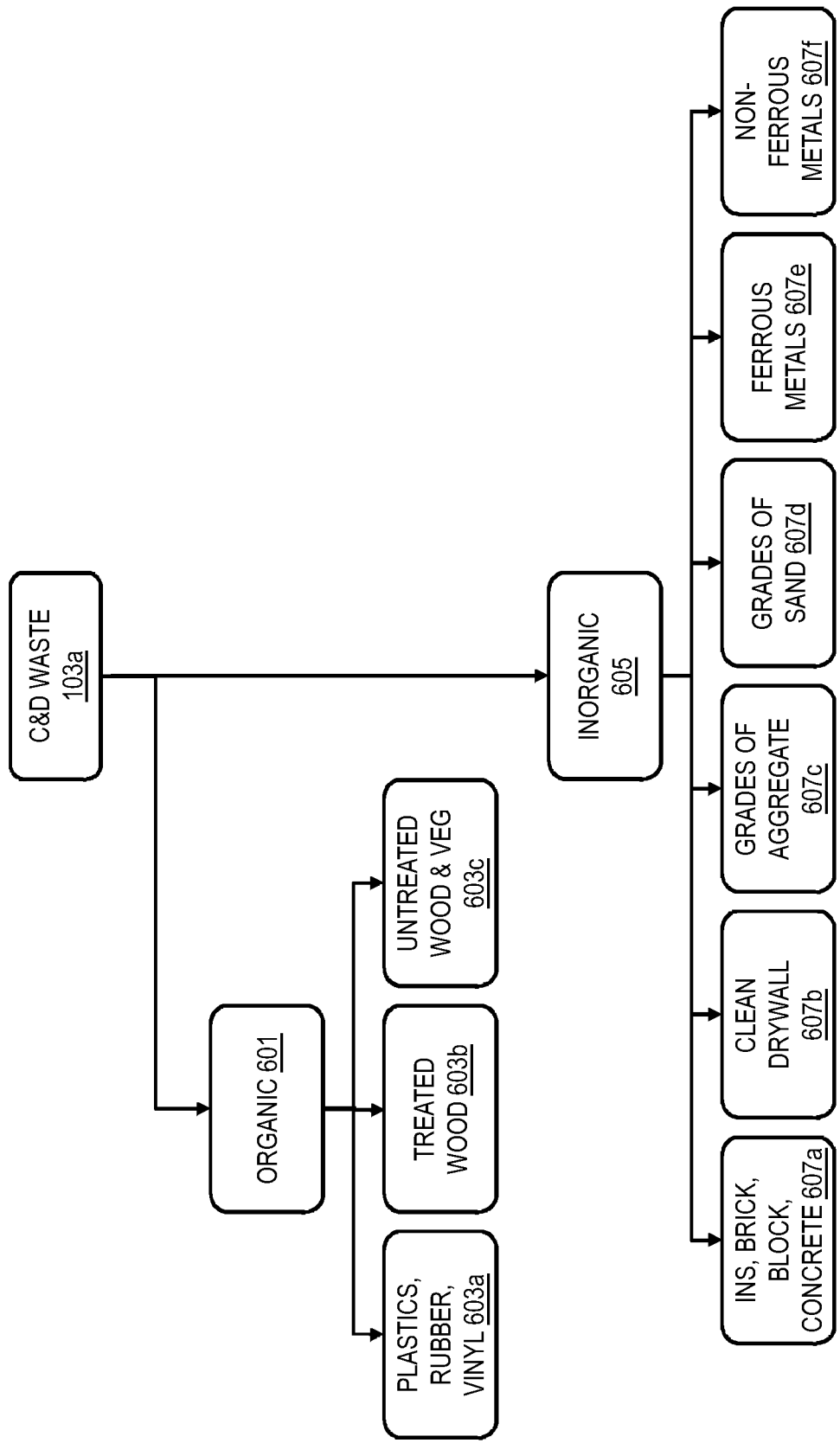
FIG. 6 is a diagram illustrating an example of using an integrated bioenergy complex to process construction and demolition ("C&D") and/or agricultural mixed solid waste, according to one embodiment.

FIG. 6 is a diagram illustrating an example of using the integrated bioenergy complex 105 to process construction and demolition ("C&D") mixed solid waste, according to one embodiment. As shown in FIG. 6, the organic waste stream 601 of C&D waste 103a includes most commonly (but not exclusively): (1) plastics, rubber, and vinyl 603a (e.g., floor covering, etc.); (2) treated wood 603b; and (3) untreated wood/vegetative materials 603c. The inorganic waste stream 605 includes commonly (but not exclusively): (1) insulation, brick, block, and concrete 607a; (2) clean drywall 607b; (3) grades of aggregate 607c; (4) grades of sand 607d; (5) ferrous metals 607e; and (6) non-ferrous metals 607f. In one embodiment, the C&D waste 103a can also include a subcategory of agricultural wastes 103f (e.g., from commercial farms). Common examples of agricultural wastes 103f can include but are not limited to plastic film used to keep weeds down in growing crops, grain straw that can no longer be burned off of fields, spoiled fruits/vegetables, vines/tree trimmings, and/or other wastes that otherwise would be landfilled. In one embodiment, all incoming C&D waste 103a will be processed and utilized through a series of separation processes of the integrated bioenergy complex 105 as described above. In one embodiment, the processes can be: (1) environmentally best of class (e.g., approved by industry groups, demonstrated to have a high level of performance, etc.), and (2) independently certified as Leadership in Energy and Environmental Design (LEED) qualified recycling/re-use or equivalent. In addition, the process design can minimize moisture content of C&D waste 103a with a blended moisture target of 10% or less.

In one embodiment, the integrated bioenergy complex 105 can transform the organic materials 601 of the C&D wastes 103a into a series of useful products:

Organic materials will be transformed into a series of useful products:
Plastics with a commercial recycling value will be baled for recycling;
Should commercial recycling value fall below the value of these plastics in producing fuels, they will be routed to the production of renewable fuels and other valuable products;
Paper/cardboard will be recycled to the extent economic with the balance used in the production of renewable fuels and other valuable products;
Carpeting and other organic floor coverings will be shredded and used in the production of renewable fuels and other valuable products;
Rubber will be shredded and dedicated to the production of renewable fuels and other valuable products; and
Woody materials—pressure treated (PT), non-treated, vegetative materials (veg)—will be ground and mechanically dried to below 10% moisture and dedicated to the production of renewable fuels and other valuable products.

Similarly, inorganic materials 605 will be transformed into a series of useful products:
Through a series of separation, recycling, and recovery techniques as discussed above, the following useful materials can be produced:
Ferrous metals will be separated for recycling;
Non-ferrous metals will be separated for recycling;
Several grades of sand and aggregates will be separated for use in the construction industry;
Silt residuals will be separated to be used as amendment in landscaping and agricultural industries;
A nominal amount of organics can emerge from this step which will be dried to less than 10% moisture and be dedicated to the production of renewable fuels and other valuable products;
Insulation, brick, block and concrete will be crushed for use in the production of insulation;
Clean drywall to be pelletized for a soil amendment; and
Ceiling tiles will be recycled back to their original use through collection at the source.

The total residual waste expected from processing all C&D waste 103 is generally less than 3%.

Figure 7:
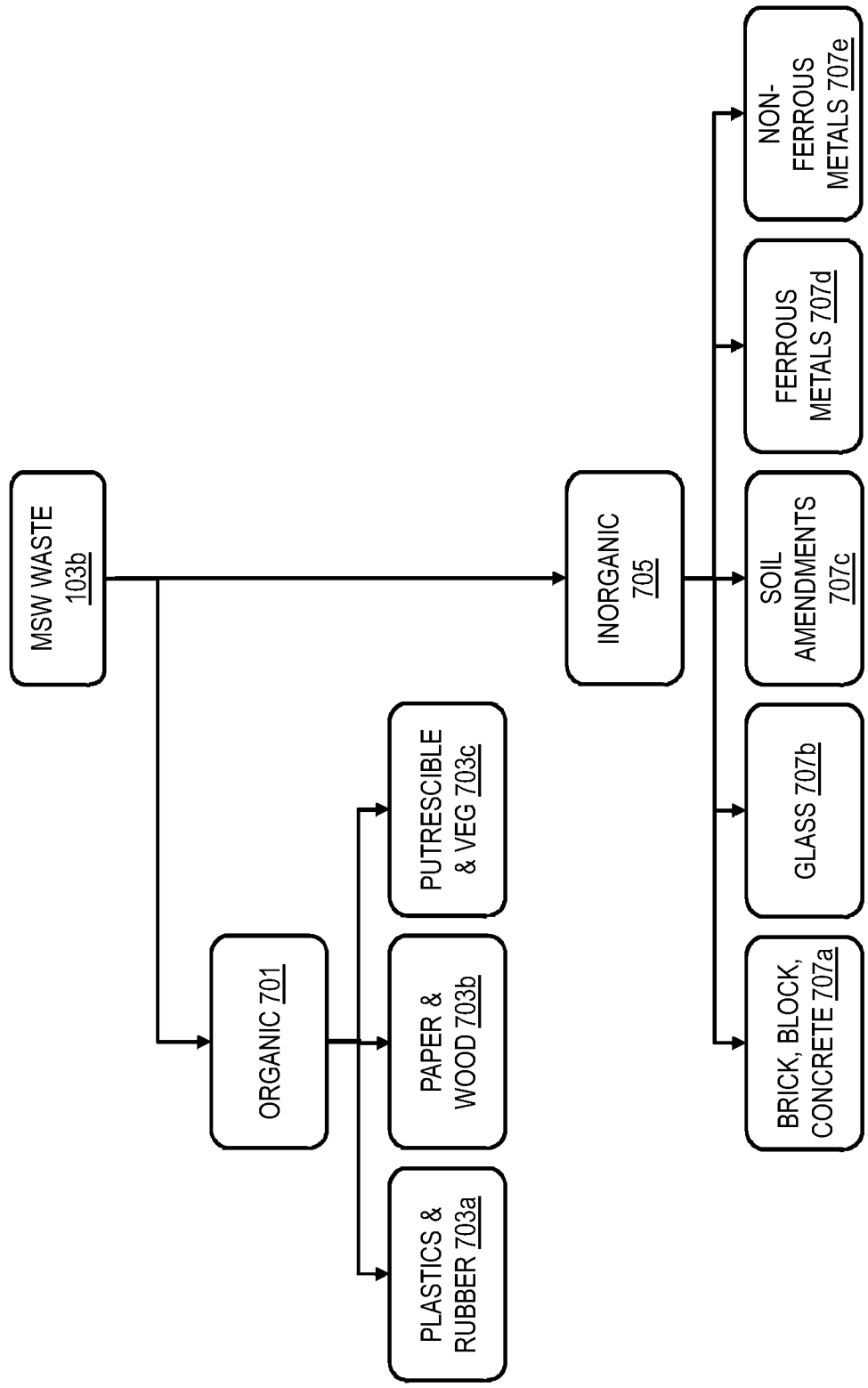
FIG. 7 is a diagram illustrating an example of using an integrated bioenergy complex to process municipal solid waste (MSW), according to one embodiment.

FIG. 7 is a diagram illustrating an example of using an integrated bioenergy complex to process municipal solid waste (MSW), according to one embodiment. As shown in FIG. 7, the organic waste stream 701 of MSW waste 103b includes most commonly (but not exclusively): (1) plastics and rubber 703a; (2) paper and wood 703b; and (3) putrescibles and vegetative materials 703c. The inorganic waste stream 705 includes commonly (but not exclusively): (1) brick, block, and concrete 707a; (2) glass 707b; (3) soil amendments 707c; (4) ferrous metals 707d; and (5) non-ferrous metals 707e. In one embodiment, all incoming MSW waste 103b will be processed and utilized through a series of separation processes of the integrated bioenergy complex 105 as described above. In one embodiment, the processes can be: (1) environmentally best of class (e.g., approved by industry groups, demonstrated to have a high level of performance, etc.), and (2) designed to optimize recycling and/or re-use. In addition, the process design can minimize moisture content of MSW waste 103b with a blended moisture target of 10% or less.

Organic materials 701 will be transformed into a series of useful products:
  Plastics with a commercial recycling value will be baled for recycling;
  Should commercial recycling value fall below the value of these plastics in producing fuels, they will be routed to the production of renewable fuels and other valuable products;
  All other non-putrescible organics will be dedicated to the production of renewable fuels and other valuable products;
  Rubber will be shredded and dedicated to the production of renewable fuels and other valuable products; and
  Putrescibles (e.g., foods, diapers, etc.) and vegetative wastes will be ground and mechanically dried to below 10% moisture and dedicated to the production of insulation and power.

Inorganic materials 705 will be transformed into a series of useful products:
  Through a series of separation techniques, the following useful materials will be produced:
    Ferrous metals will be separated for recycling;
    Non-ferrous metals will be separated for recycling;
    Several grades of sand will be separated from any 'grit' in the MSW for use in the construction industry;
    Soil residuals will be separated to be used as amendment in landscaping and agricultural industries; and
    A nominal amount of organics will emerge from this step which will be dried to less than 10% moisture and be dedicated to the production of renewable fuels and other valuable products;
  All glass, not now commercially recyclable, will be dedicated to the production of insulation; and
  Insulation, brick, block and concrete will be processes for use in the production of insulation.

The total residual waste expected from processing all MSW waste 103b is generally less 3%.

Figure 8:
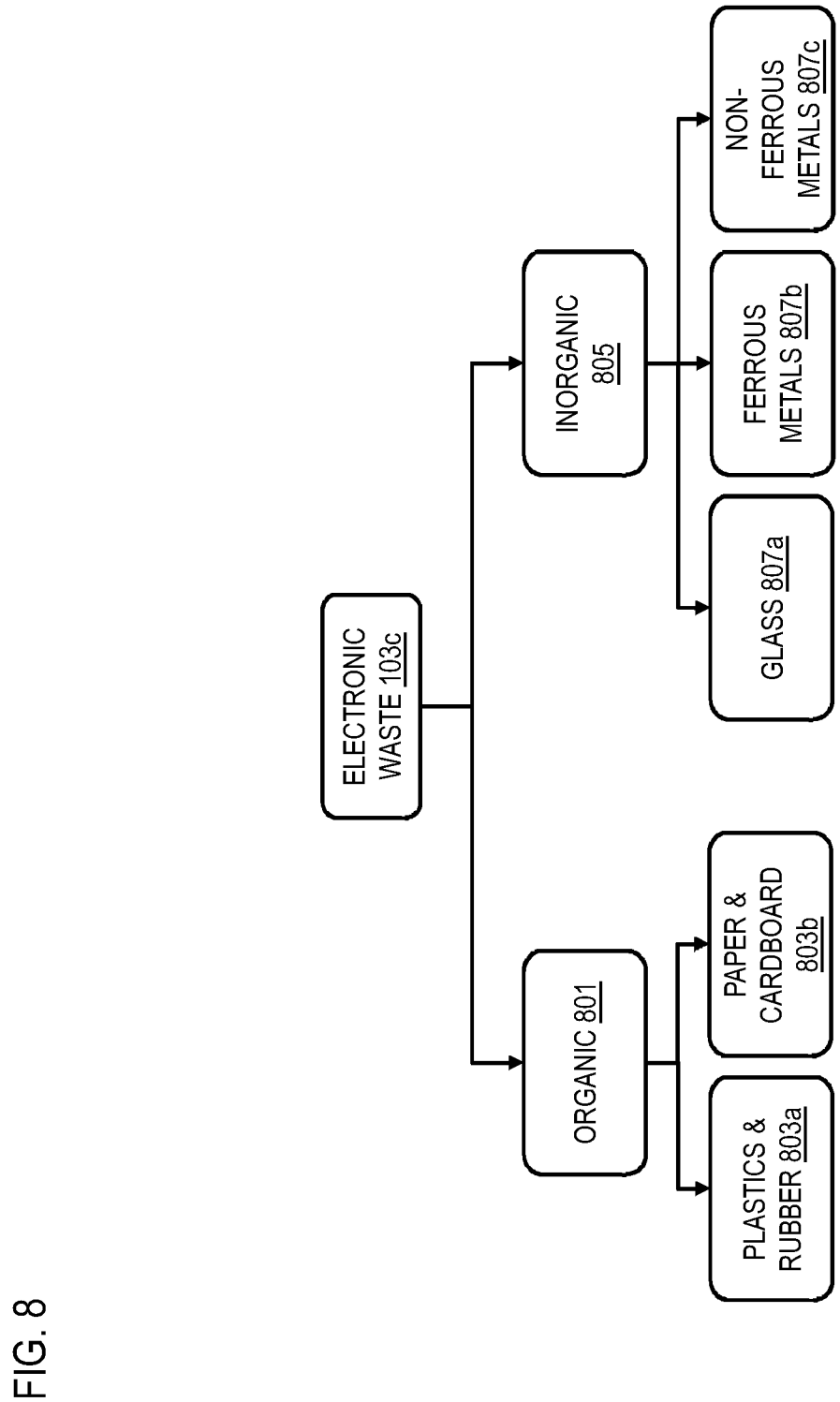
FIG. 8 is a diagram illustrating an example of using an integrated bioenergy complex to process electronic solid waste, according to one embodiment.

FIG. 8 is a diagram illustrating an example of using an integrated bioenergy complex to process electronic solid waste, according to one embodiment. As shown in FIG. 8, the organic waste stream 801 of electronic waste 103c includes most commonly (but not exclusively): (1) plastics and rubber 803a; and (2) paper and cardboard 803b. The inorganic waste stream 805 includes commonly (but not exclusively): (1) glass 807a; (2) ferrous metals 807b; and (3) non-ferrous metals 807c. In one embodiment, all incoming electronic waste 103c will be processed and utilized through a series of separation processes of the integrated bioenergy complex 105 as described above. In one embodiment, the processes can be: (1) environmentally best of class (e.g., approved by industry groups, demonstrated to have a high level of performance, etc.), and (2) designed to optimize recycling and/or re-use. In addition, the process design can minimize moisture content of electronic waste 103c with a blended moisture target of 10% or less.

Organic materials 801 can be transformed into a series of useful products:
  Plastics with a commercial recycling value can be baled for recycling;
  Should commercial recycling value fall below the value of these plastics in producing fuels, they can be dedicated to producing renewable fuels and other valuable products;
  All other non-putrescible organics (paper, plastics, wood pallets, etc.) can be dedicated to the production of renewable fuels, insulation, power and other valuable products;
  Plastic and rubber can be shredded and dedicated to the production of renewable fuels and other valuable products.

Inorganic materials 805 can be transformed into a series of useful products:
  The following materials can be recycled through a series of separation methods:
    Ferrous metals can be separated for recycling;
    All copper that can be economically separated can be collected for recycling;
    Other recyclable metals that can be economically separated can be collected for recycling;
  Through a series of separation techniques, the following useful materials can be produced:
    Non-ferrous metals (gold, platinum, silver, copper and others) can be transformed to ingots to be heat separated at a later time for recycling;
    A nominal amount of organics can emerge from this step which can be dried to less than 10% moisture and be dedicated to the production of renewable fuels and other valuable products.

The total residual waste expected from processing all electronic waste 103a is generally less 3%.

Figure 9:
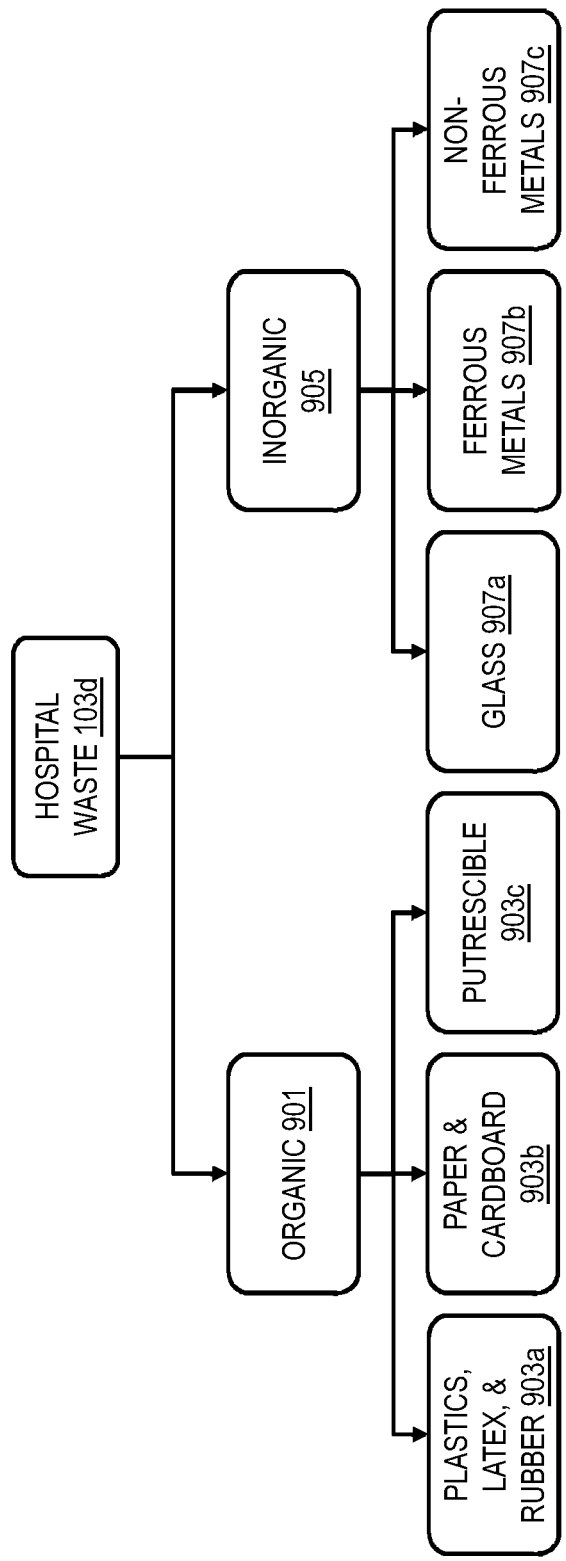
FIG. 9 is a diagram illustrating an example of using an integrated bioenergy complex to process hospital or medical solid waste, according to one embodiment.

FIG. 9 is a diagram illustrating an example of using an integrated bioenergy complex to process hospital or medical solid waste, according to one embodiment. As shown in FIG. 9, the organic waste stream 901 of hospital waste 103e includes most commonly (but not exclusively): (1) plastics, latex, and rubber 903a; (2) paper and cardboard 903b; and (3) putrescibles 903c. The inorganic waste stream 805 includes commonly (but not exclusively): (1) glass 907a; (2) ferrous metals 907b; and (3) non-ferrous metals 907c. In one embodiment, all incoming hospital waste 103d will be processed and utilized through a series of separation processes of the integrated bioenergy complex 105 as described above. In one embodiment, the processes can be: (1) environmentally best of class (e.g., approved by industry groups, demonstrated to have a high level of performance, etc.), and (2) designed to optimize recycling and/or re-use. In addition, the process design can minimize moisture content of MSW waste 103b with a blended moisture target of 10% or less.

Organic materials 901 will be transformed into a series of useful products:
  Plastics can be hermetically handled and delivered to a 1,400° F. (+/−) thermal cracking system in order to produce fuels, they can be dedicated to producing renewable fuels and other valuable products;
  All other non-putrescible organics (paper, plastics, wood pallets, etc.) can be dedicated to the same type of thermal cracking to production of renewable fuels, insulation, power and other valuable products; and
  Plastic and rubber will be dedicated to the thermal cracking process for the production of renewable fuels and other valuable products.

In one embodiment, inorganic materials 905 can first be subjected to a 1,400°+/−F thermal cracking system for sterilization. Thereafter, inorganic materials 905 can be transformed into a series of useful products:

Glass can be used for the production of fiberglass;
The following materials can be recycled through a series of separation methods:
Ferrous metals can be separated for recycling; and
Other recyclable metals that can be economically separated can be collected for recycling.

The total residual waste expected from processing all hospital waste 103d is generally less than 3%.

Figure 10:
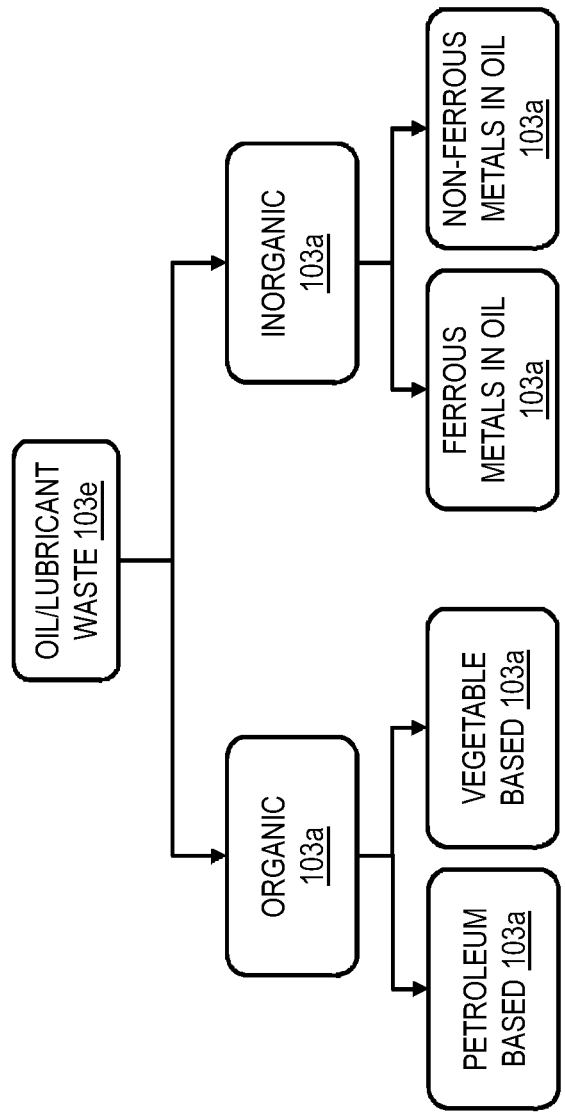
FIG. 10 is a diagram illustrating an example of using an integrated bioenergy complex to process oil/lubricant solid waste, according to one embodiment.

FIG. 10 is a diagram illustrating an example of using an integrated bioenergy complex to process oil/lubricant solid waste, according to one embodiment. As shown in FIG. 10, the organic waste stream 1001 of oil/lubricant waste 103e includes most commonly (but not exclusively): (1) petroleum-based oils and lubricants 1003a; and (2) vegetable-based oils and lubricants 1003b. The inorganic waste stream 1005 includes commonly (but not exclusively): (2) ferrous metals in oil 1007a; and (3) non-ferrous metals in oils 1007b. In one embodiment, all incoming oil/lubricant waste 103e can be processed and utilized through a series of separation processes of the integrated bioenergy complex 105 as described above. In one embodiment, the processes can be: (1) environmentally best of class (e.g., approved by industry groups, demonstrated to have a high level of performance, etc.), and (2) designed to optimize recycling and/or re-use. In addition, care can be taken to minimize any contamination by water with these materials.

In one embodiment, all of this organic and inorganic materials 1001 and 1005 (e.g., motor oils, lubricants, vegetable oils, oil contaminated soils, fuel contaminated soils, etc.) can be blended with the organic materials from processing other waste types as described above for feeding into the organic conversion processing center 107a to form liquid fuels and other valuable products. Generally, there will be a number of inorganic materials 1005 within these oils and lubricants (e.g., engine filings, engine wear items, etc.). These inorganic materials will be resident in the ash (i.e., residuals from the organic conversion processing center 107a) arising from the organic conversion processing center 107a, and will be formed into ingots by the inorganic conversion processing center 107b.

The total residual waste expected from processing all oil/lubricant waste 103e is generally less than 1%.

Figure 11:
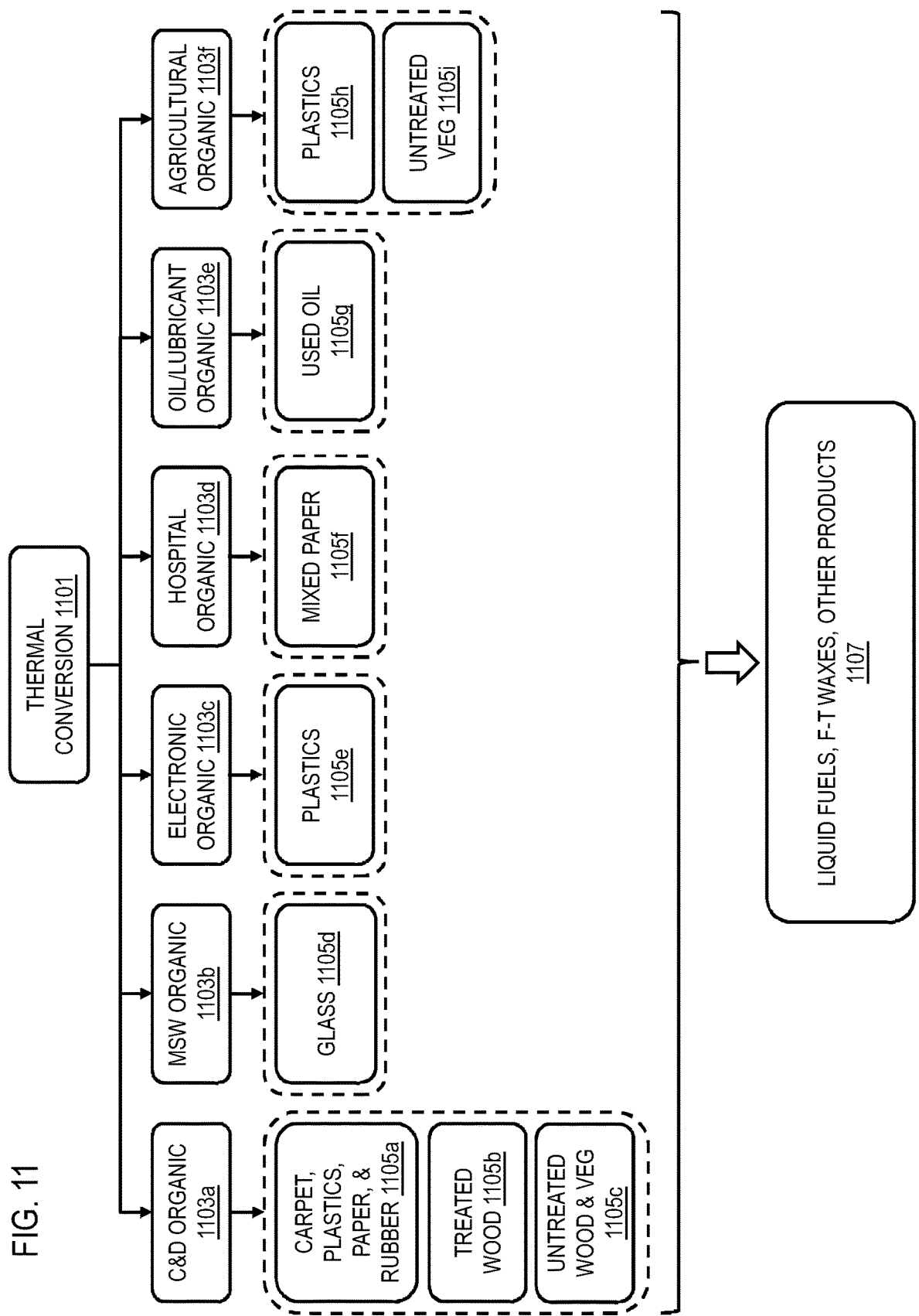
FIG. 11 is a diagram illustrating example organic conversion products generated from organic waste streams, according to one embodiment.

FIG. 11 is a diagram illustrating example organic conversion products generated from organic waste streams, according to one embodiment. More specifically, FIG. 11 summarizes the products that result from using a thermal conversion process 1101 (e.g., by the organic conversion processing center 107a) to process the organic waste streams of across different waste types. These waste types include, for instance: (1) C&D organic stream 1103a consisting of, e.g., carpet/plastics/paper/rubber 1105a, treated wood 1105b, and untreated wood/veg 1105c; (2) MSW organic stream 1103b consisting of, e.g., plastics/paper/rubber 1105d; (3) electronic organic stream 1103c consisting of, e.g., plastics 1105e; (4) hospital organic stream 1103d consisting of, e.g., mixed paper 1105f; (5) oil/lubricant organic stream 1103e consisting of, e.g., used oil 1105g; and (6) agricultural organic stream 1103f consisting of, e.g., plastics 1105h and untreated veg 1105i. In one embodiment, the thermal conversion process 1101 can be: (1) environmentally best of class (e.g., approved by industry groups, demonstrated to have a high level of performance, etc.), and (2) designed to optimize recycling and/or re-use. For example, the embodiments described herein can use a thermal conversion process 1101 that is able to sequester approximately one ton $CO_2$ equivalents for every ton of mixed solid waste 101 processed, thereby reducing the carbon footprint of the integrated bioenergy complex 105. In addition, the process design can minimize moisture content of MSW waste 103b with a blended moisture target of 10% or less.

The organic materials can be transformed into a series of useful products 1107:
High grade (ASTM quality) diesel fuel with extremely low levels of both contaminants and sulfur;
High grade (ASTM quality) jet fuel with extremely low levels of contaminants;
High grade (ASTM) quality) solvents and naphtha with extremely low levels of contaminants;
High grade (ASTM quality) gasoline with extremely low levels of contaminants;
High grade (ASTM quality) ethanol with extremely low levels of contaminants;
High grade ethylene with extremely low levels of contaminants;
Fischer-Tropsch waxes with extremely low levels of contaminants; and
Other intermediate chemicals and liquids that have extremely low levels of contaminants and high value in commercial use.

The total residual waste expected from all these organics thermally cracked is estimated to be less than 3%.

Figure 12:
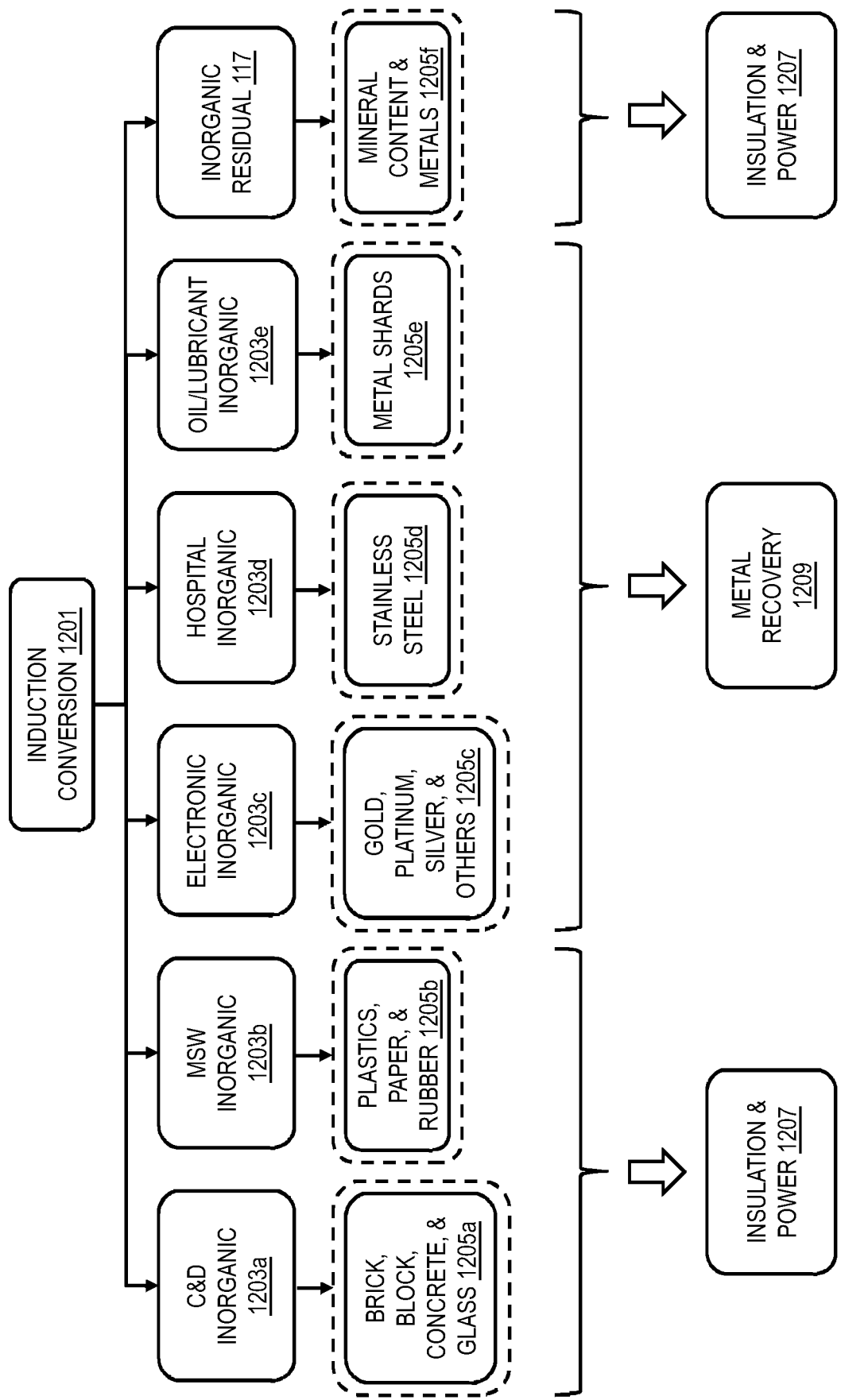
FIG. 12 is a diagram illustrating example organic conversion products generated from organic waste streams, according to one embodiment.

FIG. 12 is a diagram illustrating example inorganic conversion products generated from inorganic waste streams, according to one embodiment. More specifically, FIG. 12 summarizes the products that result from using an induction conversion process 1201 (e.g., by the inorganic conversion processing center 107b) to process the inorganic waste streams of across different waste types. These waste types include, for instance: (1) C&D inorganic stream 1203a consisting of, e.g., brick/block/concrete/glass 1205a; (2) MSW inorganic stream 1203b consisting of, e.g., glass 1205b; (3) electronic inorganic stream 1203c consisting of, e.g., gold/platinum/silver/others 1205c; (4) hospital inorganic stream 1203d consisting of, e.g., stainless steel 1205d; (5) oil/lubricant inorganic stream 1203e consisting of, e.g., metal shards 1205e; and (6) inorganic residual 117 consisting of, e.g., mineral content/metals 1205f in the ash from the organic conversion processing center 107a. In one embodiment, the induction conversion process 1201 can be: (1) environmentally best of class (e.g., approved by industry groups, demonstrated to have a high level of performance, etc.), and (2) designed to optimize recycling and/or re-use. In addition, the process design can minimize moisture content of MSW waste 103b with a blended moisture target of 10% or less.

Inorganic materials will be transformed into a series of useful products:
C&D inorganic stream 1203a and MSW inorganic 1203b can used to generate insulation and electric power 1207 using the induction conversion 1201 of the inorganic conversion processing center 107b;
Electronic inorganic stream 1203c, hospital inorganic stream 1203d, and oil/lubricant inorganic stream 1203e can be process for metal recovery 1209 using the induction conversion 1201 of the inorganic conversion processing center 107b;
Inorganic residual 117 is the remaining inorganics from the organic conversion processing center 107a, e.g., residual ash in the bottom of the thermal cracker, and is processed to generate insulation/power 1207 and/or metal recovery 1209 as follows:
Nominal amounts of ferrous and non-ferrous metals can be present in the ash of the thermal cracker;

Nominal amounts of glass can be present in the ash of the thermal cracker;

The mineral content from all of the consumed organic materials can remain in the ash; and In one embodiment, it is contemplated that there are no remaining organic residuals after processing through inorganic conversion processing center 107b because of aggressive thermal induction/plasma converter treatment. However, if a nominal amount of organics emerges from this step, any remaining organic residuals can be dried to less than 10% moisture and then dedicated to the production of renewable fuels and other valuable products.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged and/or re-arranged in any combination and order.

What is claimed is:

1. A method for processing mixed solid waste comprising:
   receiving the mixed solid waste at an integrated bioenergy complex, the integrated bioenergy complex including an organic conversion processing center and an inorganic conversion processing center;
   separating the mixed solid waste into an organic waste stream and an inorganic waste stream;
   feeding the organic waste stream to the organic conversion processing center to produce one or more organic conversion products and a first residual;
   feeding the first residual and the inorganic waste stream to the inorganic conversion processing center to produce one or more inorganic conversion products, electric power, and a second residual; and
   cross-feeding the first residual from the organic conversion processing center to the inorganic conversion processing center and the second residual from the inorganic processing center to the organic conversion processing center until a target residual percentage is below a target threshold,
   wherein the electric power is used to partially or fully power the organic conversion processing center.

2. The method of claim 1, further comprising:
   processing the mixed solid waste to achieve a blended moisture content less than or equal to a target moisture percentage.

3. The method of claim 2, wherein the target moisture percentage is 10%, and wherein the target residual percentage of the received mixed solid waste is 3% or less.

4. The method of claim 1, further comprising:
   prior to feeding the organic waste stream to the organic conversion processing center and the inorganic waste stream, to the inorganic conversion processing center, extracting a recyclable material from the organic waste stream or the inorganic waste stream when a commercial value of the recyclable material is greater than a commercial value threshold.

5. The method of claim 1, wherein the recyclable material includes plastic, paper/cardboard, metals, sand, aggregates, silt, or a combination thereof.

6. The method of claim 1, wherein the organic conversion processing center includes a liquid fuels plant to produce the one or more organic conversion products from the organic waste stream.

7. The method of claim 6, wherein the organic residual is ash resulting from the liquid fuels plant.

8. The method of claim 6, further comprising:
   using a thermal process of the liquid fuels plant to sterilize the inorganic waste stream prior to feeding the inorganic waste stream to the inorganic conversion processing center.

9. The method of claim 1, wherein the inorganic conversion processing center includes an insulation/power plant to produce the one or more or more inorganic conversion products, the electric power, the residual waste, or a combination thereof from the inorganic waste stream.

10. The method of claim 9, wherein the one or more organic conversion products are fed to the inorganic conversion processing center as fuel for the insulation/power plant.

11. The method of claim 1, further comprising:
    using process heat collected from the organic conversion processing center, the inorganic conversion processing center, or a combination thereof to dry the mixed solid waste to achieve the target moisture percentage.

12. The method of claim 1, further comprising:
    using process heat collected from the organic conversion processing center, the inorganic conversion processing center, or a combination thereof to operate a steam generator system.

13. The method of claim 1, wherein the one or more organic conversion products include diesel fuel, jet fuel, organic solvents, naphtha, gasoline, ethanol, ethylene, Fischer-Tropsch waxes, or a combination thereof; and wherein the one or more inorganic conversion products include rock wool, metal ingots, green electric power or a combination thereof.

14. The method of claim 1, wherein the mixed solid waste includes construction and demolition waste, vegetative waste, agricultural waste, municipal solid waste, electronic waste, hospital waste, waste oil, oil-contaminated waste, lubricant waste, or a combination thereof.

* * * * *